(12) United States Patent
Arai et al.

(10) Patent No.: US 6,620,096 B2
(45) Date of Patent: Sep. 16, 2003

(54) TUBE CONNECTING STRUCTURE OF ENDOSCOPE

(75) Inventors: Hiroyuki Arai, Saitama (JP); Tetsuya Fujikura, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 24 days.

(21) Appl. No.: 09/961,339

(22) Filed: Sep. 25, 2001

(65) Prior Publication Data
US 2002/0040181 A1 Apr. 4, 2002

(30) Foreign Application Priority Data
Sep. 29, 2000 (JP) .......................... 2000-298209

(51) Int. Cl.$^7$ .............................. A61B 1/12; A61B 1/00
(52) U.S. Cl. ....................... 600/156; 600/130
(58) Field of Search ............................... 600/156, 153, 600/157, 158, 159, 130, 101; 604/533, 284

(56) References Cited

U.S. PATENT DOCUMENTS

| 4,860,731 A | * | 8/1989 | Matsuura ..................... 600/157 |
| 5,840,016 A | * | 11/1998 | Kitano et al. ............... 600/159 |
| 6,425,535 B1 | * | 7/2002 | Akiba ......................... 239/369 |

FOREIGN PATENT DOCUMENTS

JP   11-253393   9/1999

* cited by examiner

Primary Examiner—Linda C. M. Dvorak
Assistant Examiner—Kenneth G Schopfer
(74) Attorney, Agent, or Firm—Oliff & Berridge, PLC

(57) ABSTRACT

In a tube connecting structure of an endoscope, a fluid supply tube is connected to a gas supply tube and a liquid supply tube via a tube joint. The tube joint is arranged at the inside of an insertion part of the endoscope, and is constructed of a main tube and a branch tube. The branch tube is provided next to the main tube, while an end of the branch tube protrudes to be longer than an end of the main tube.

3 Claims, 6 Drawing Sheets

TUBE CONNECTING STRUCTURE OF ENDOSCOPE

BACKGROUND OF THE INVENTION

1. Field of the Invention

The present invention relates to a tube connecting structure of an endoscope, specifically to one with a structure in which a fluid supply tube arranged through an insertion part of an endoscope is connected to a gas supply tube and a liquid supply tube via a tube joint.

2. Description of the Related Art

The distal end of the insertion part of an endoscope is provided with an observation window, through which a subject is observed, and a nozzle for jetting a gas or liquid for cleaning the observation window. A fluid supply tube for supplying the gas or liquid is connected to the nozzle. The fluid supply tube is divided at the inside of the insertion part of the endoscope into a gas supply tube for supplying gas and a liquid supply tube for supplying liquid, and the gas supply tube and the liquid supply tube are connected to a fluid supply valve, which is arranged at a hand control part of the endoscope. The gas or liquid is supplied to the liquid or gas supply tube by operating the fluid supply valve, then is jetted from the nozzle.

Japanese Patent Application Publication No. 11-253393 discloses an endoscope shown in FIG. 6, in which the fluid supply tube 5 is connected to the gas supply tube 3 and the liquid supply tube 4 through the tube joint. The tube joint is constituted of a main tube 1 and a branch tube 2, which is connected to the main tube 1, and an end 2A of the branch tube 2 is arranged adjacently to an end 1A of the main tube 1. The gas supply tube 3 is coupled with the outside of the end 2A of the branch tube 2, the liquid supply tube 4 is coupled with the outside of the end 1A of the main tube 1, and the fluid supply tube 5 is coupled with the outside of an end 1B of the main tube 1. This endoscope achieves narrowing the insertion pat by arranging the tube joint in a swollen part in between the insertion part and the hand control part in order to dispose only the fluid supply tube in the insertion part.

However, the endoscope disclosed in Japanese Patent Application Publication No. 11-253393 has a long fluid supply tube and a considerable amount of liquid or gas is left in the fluid supply tube; and hence, a gas supply operation and liquid supply operation have been difficult to switch quickly.

Moreover, the conventional tube connecting structure requires a large space d between the end 2A of the branch tube 2 and the end 1A of the main tube 1 in order to prevent the gas supply tube 3 and the liquid supply tube 4 from coming into contact with each other; and hence, the connecting part of the tubes with the tube joint must be thick. Because the connecting part of the tubes is thicker than the other parts of the endoscope, contents in the insertion part of the endoscope may become jammed, whereby they may be damaged. For that reason, narrowing the insertion part of the endoscope has been difficult to achieve.

SUMMARY OF THE INVENTION

The present invention has been developed in view of the above-described circumstances, and has as its object the provision of a tube connecting structure of an endoscope with which an insertion part can be narrowed and at the same time the gas and liquid supplies can be switched quickly In order to achieve the above-described objects, the present invention is directed to a tube connecting structure which is arranged at an insertion part of an endoscope, comprising: a tube joint which has, at a first side, a first end to which a fluid supply tube is connected, and has, at a second side, a second end to which a gas supply tube is connected and a third end to which a liquid supply tube is connected, wherein a position at which the gas supply tube is connected to the second end and a position at which the liquid supply tube is connected to the third end are differ in a longitudinal direction of the tube joint.

According to the present invention, since a position at which the gas supply tube is connected to the tube end and a position at which the liquid supply tube is connected to the tube end are located at different positions in a longitudinal direction of the tube joint, the connecting part of the gas supply tube and the connecting part of the liquid supply tube do not interfere with each other. Thus, the space between the ends of the two tubes can be narrowed which causes the tube connecting part to be narrowed; as a result, the tools inside the insertion part are not jammed. Therefore, durability of the tools improves and at the same time the insertion part is further narrowed.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENTS

Hereunder a preferred embodiment of a tube connecting structure of the present invention will be described in detail in accordance with the accompanying drawings.

Figure 1:
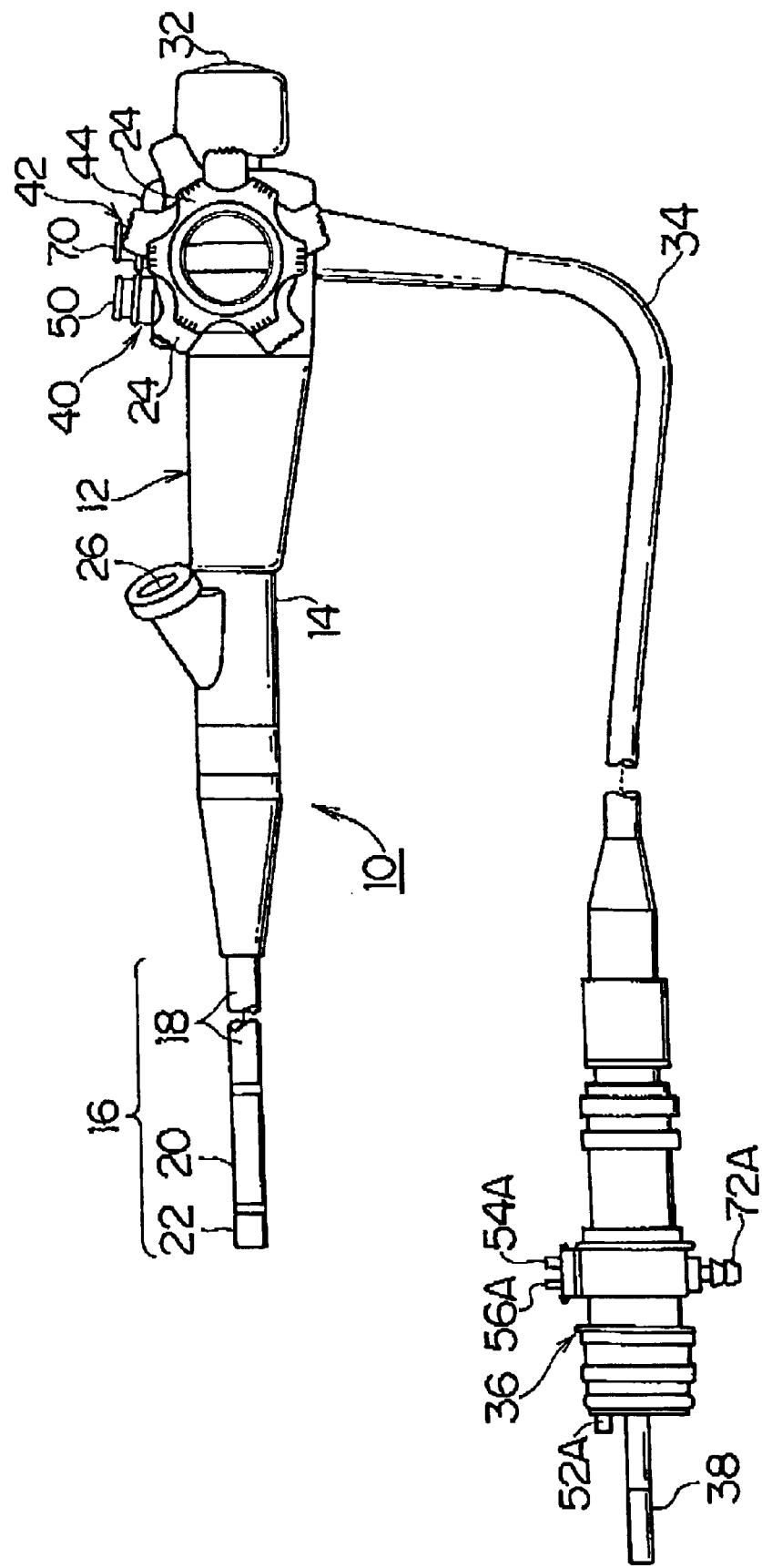
FIG. 1 is a view of an entire endoscope to which a tube connecting structure of the present invention is applied.

An endoscope 10 in FIG. 1 to which a tube connecting structure according to an embodiment of the present invention is applied has a hand control part 12 and an insertion part 16, which is connected to a joint 14 of the hand control part 12. The insertion part 16 comprises a flexible part 18, a bending part 20, and a distal end part 22. The bending part 20 is connected to a pair of angle operation knobs 24 provided to the hand control part 12 via angle operating wires (not shown), which are arranged through the flexible part 18. When the angle operating knobs 24 are operated by the user, the bending part 20 is bent and the distal end part 22 is pointed at a desired direction. The joint 14 has a forceps inlet 26, through which a surgical tool such as forceps is inserted into the insertion part 16.

Figure 2:
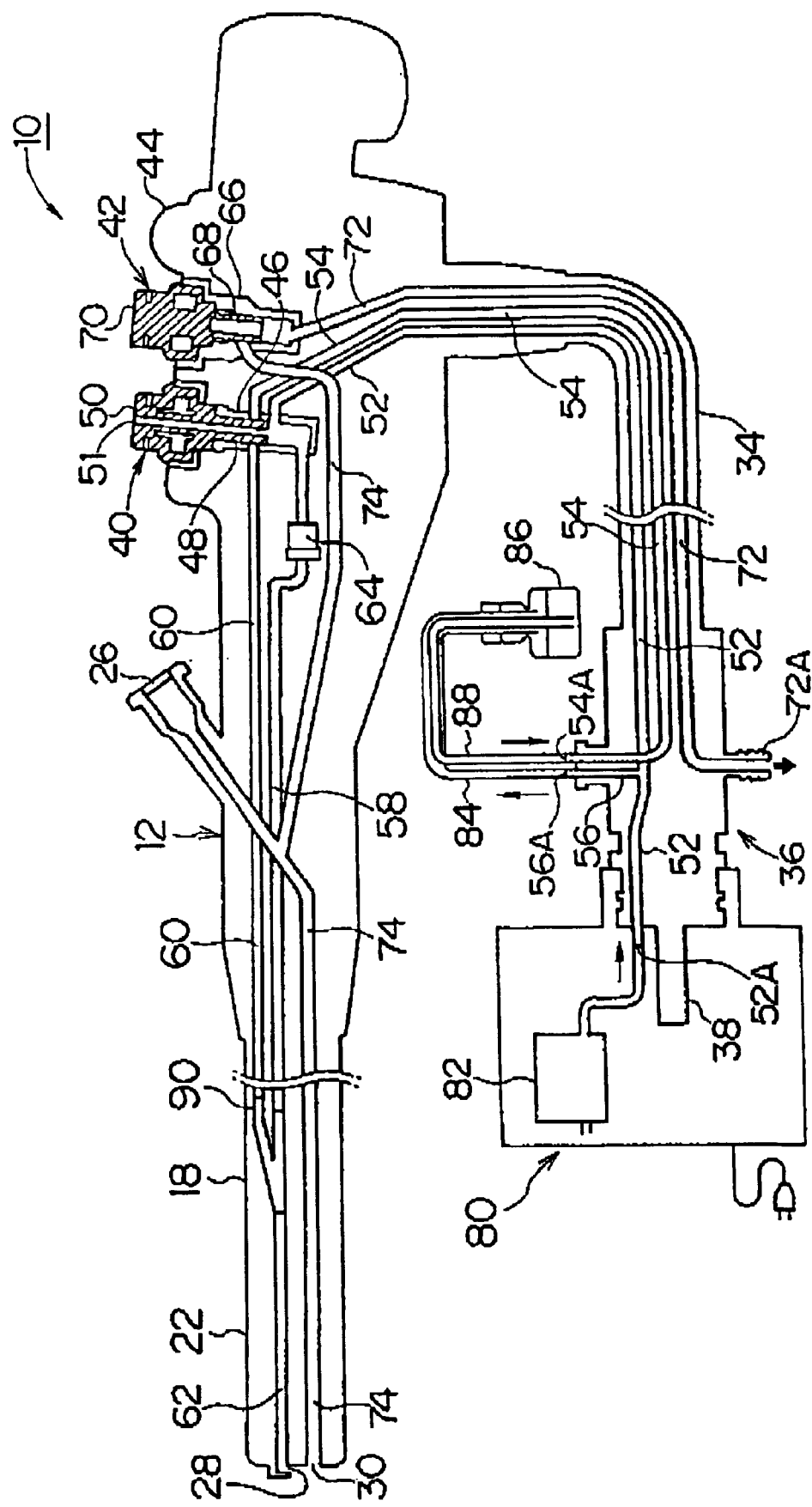
FIG. 2 is a model view showing plural tube routes provided in the endoscope in FIG. 1.

As seen from FIG. 2, a fluid spout 28 and a forceps channel 30 are formed at an end face of the distal end part 22. The distal end part 22 further has an objective lens and an illumination lens (not shown) adjacent to the fluid spout 28 and the forceps channel 30.

A light guide (not shown) is provided at the back of the illumination lens. The light guide is arranged through the bending part 20, the flexible part 18, the hand control part 12 and a flexible cable 34, and is connected to a light guide stick 38 of a light guide connector 36.

When the endoscope 10 is used, the light guide connector 36 is connected to a light source device 80 in FIG. 2, and the light guide stick 38 is connected to a light source (not shown) of the light source device 80; thereby, the light from the light source is emitted to the subject through the light guide stick 38, the light guide and the illumination lens.

The hand control part 12 is provided with a fluid supply valve 40, and a suction valve 42 and a shutter button 44 are arranged adjacently to the fluid supply valve 40.

The fluid supply valve 40 comprises a cylinder 46, a piston 48 and an operation button 50, Respective ends of a gas tube 52 and a liquid tube 54 are connected to the cylinder 46. The gas tube 52 is extended to the light guide connector 36 through the flexible cable 34, and a connecting end 52A protrudes from the light guide connector 36. When the light guide connector 36 is connected to the light source device 80, the connecting end 52A is connected to a pump 82, which is built in the light source device 80. The gas (e.g., air) is supplied from the pump 82 to the cylinder 46 through the gas tube 52. The gas supplied to the cylinder 46 is supplied to a gas supply tube 58 by blocking a gas leaking hole 51 formed on the operation button 50 with the user's finger.

The gas tube 52 is connected to a branch tube 56 in the inside of the light guide connector 36. A connecting end 56A of the branch tube 56 protrudes from the light guide connector 36, and is connected to a liquid tank 86, which contains a liquid (e.g., water). The liquid tank 86 is connected to a liquid supply tube 88, which is connected to a connecting end 54A of the liquid tube 54, which protrudes from the light guide connector 36. Therefore, when the piston 48 is pressed while the gas leaking hole 51 of the fluid supply valve 40 is blocked, the gas supplied from the pump 82 flows into the branch tube 56 and is jetted to the liquid tank 86 through the gas supply tube 84. As such, an internal pressure of the liquid tank 86 increases, and the liquid within the liquid tank 86 flows into the liquid tube 54 through the liquid supply tube 88, then the liquid is supplied to the cylinder 46. The liquid supplied to the cylinder 46 is supplied to a liquid supply tube 60 by pressing the piston 48 while blocking the gas leaking hole 51.

Respective proximal ends of the gas supply tube 58 and the liquid supply tube 60 are connected to respective positions of the cylinder 46, and respective distal ends of the gas supply tube 58 and the liquid supply tube 60 are connected to a single fluid supply tube 62 through a tube joint 90. The fluid supply tube 62 is arranged through the insertion part 16, and is connected to the fluid spout 28, which is formed at the distal end part 22. A check valve 64 is arranged at the gas supply tube 58 in order to prevent a reverse flow of the fluid.

The suction valve 42 comprises a cylinder 66, a piston 68 and an operation button 70. The cylinder 66 is connected to the distal end of a connecting tube 72, which is extended to the light guide connector 36 through the flexible cable 34, and a connecting end 72A of the connecting tube 72 protrudes from the light guide connector 36. The connecting end 72A is connected to a suction pump (not shown).

A suction tube 74 is connected to the cylinder 66. The suction tube 74 is arranged through the insertion part 16 and is connected to the forceps channel 30, which is formed at the distal end part 22. When the piston 68 is pressed by operating the operation button 70 of the suction valve 42, the suction tube 74 is connected to the connecting tube 72 through the cylinder 66, and liquids in the subject is sucked to the suction tube 74 from the forceps channel 30, and discharged to the outside through the connecting tube 72. The forceps inlet 26 is connected to the suction tube 74 within the hand control part 12, and the suction tube 74 is used also as a tube for inserting surgical tools such as forceps.

Figure 3:
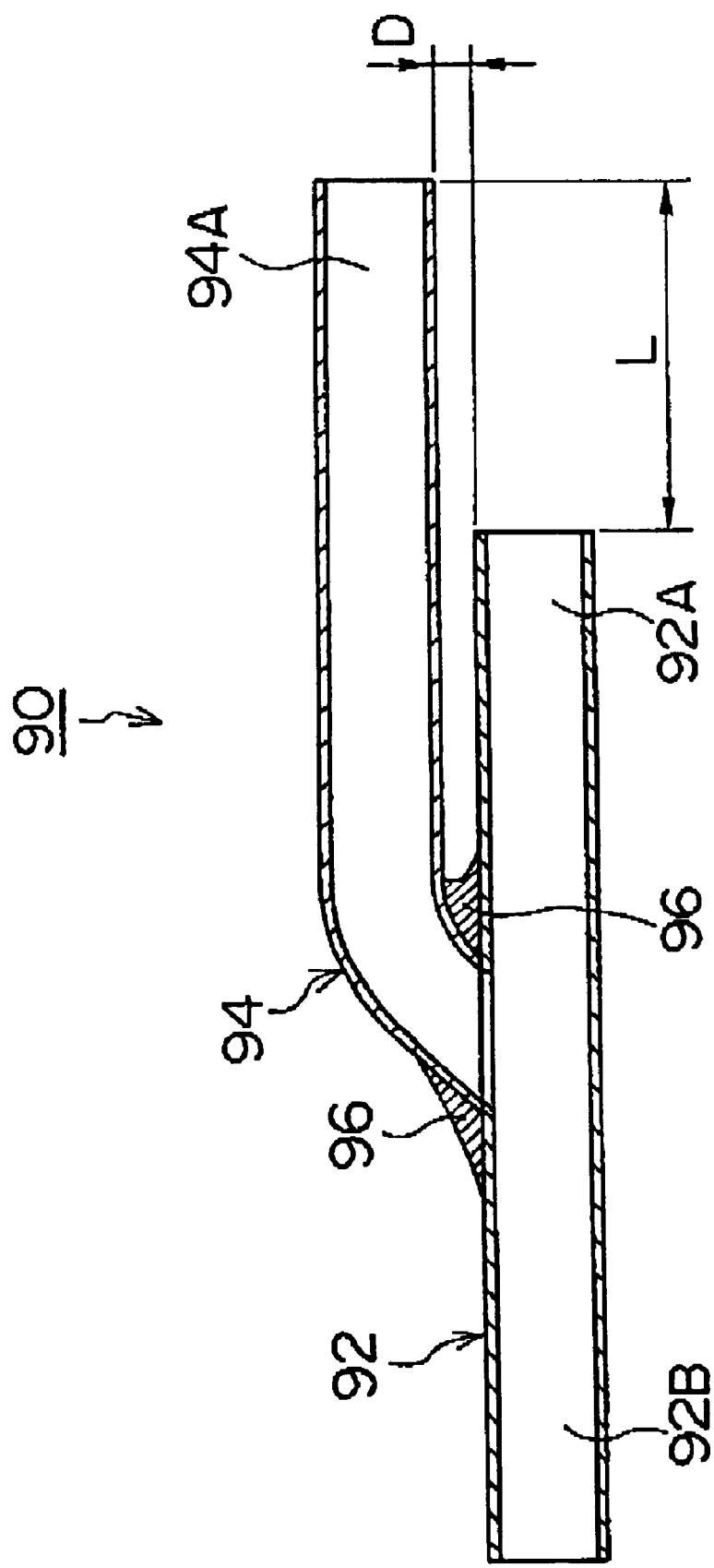
FIG. 3 is a section view of a tube joint in FIG. 2.

As seen now from FIG. 3, the tube joint 90 comprises a straight main tube 92 and a branch tube 94, which is connected to the center of the main tube 92. The branch tube 94 is obliquely connected to the main tube 92 with solder 96, and the branch tube 94 is bent at the proximity of the connecting part to be substantially parallel with the main tube 92. An end 94A of the branch tube 94 is longer than an end 92A of the main tube 92 by a length L. In other words, the ends 94A and 92A are arranged at positions that differ by the length L in a longitudinal direction. The L is a required length in order to connect the liquid supply tube 60 to the end 94A of the branch tube 94.

Figure 4:
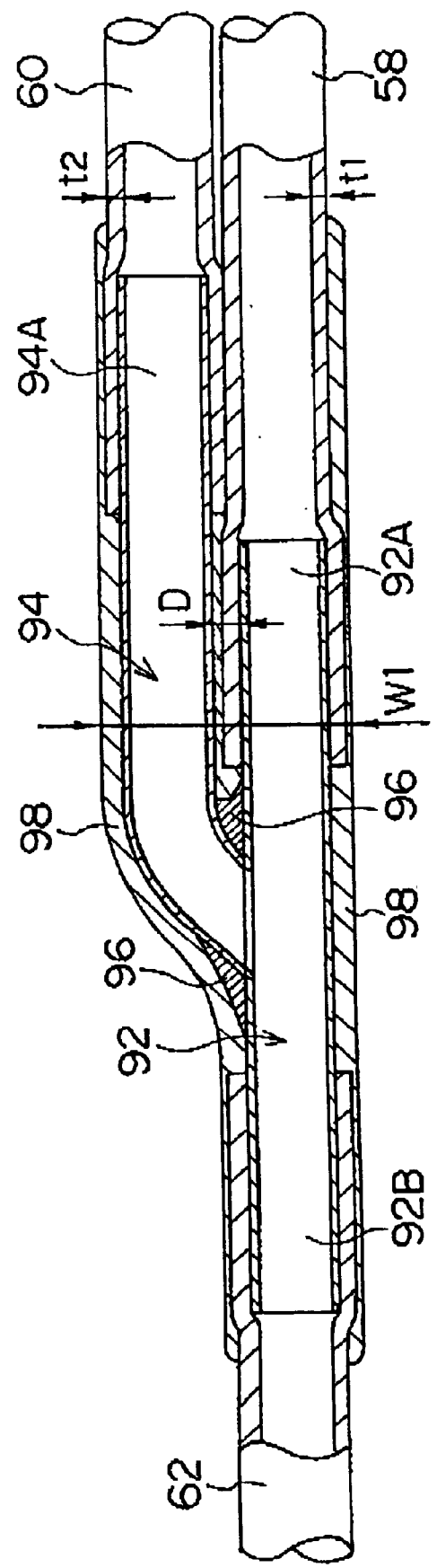
FIG. 4 is a section view of a tube connecting structure which uses the tube joint in FIG. 3.
Figure 5:
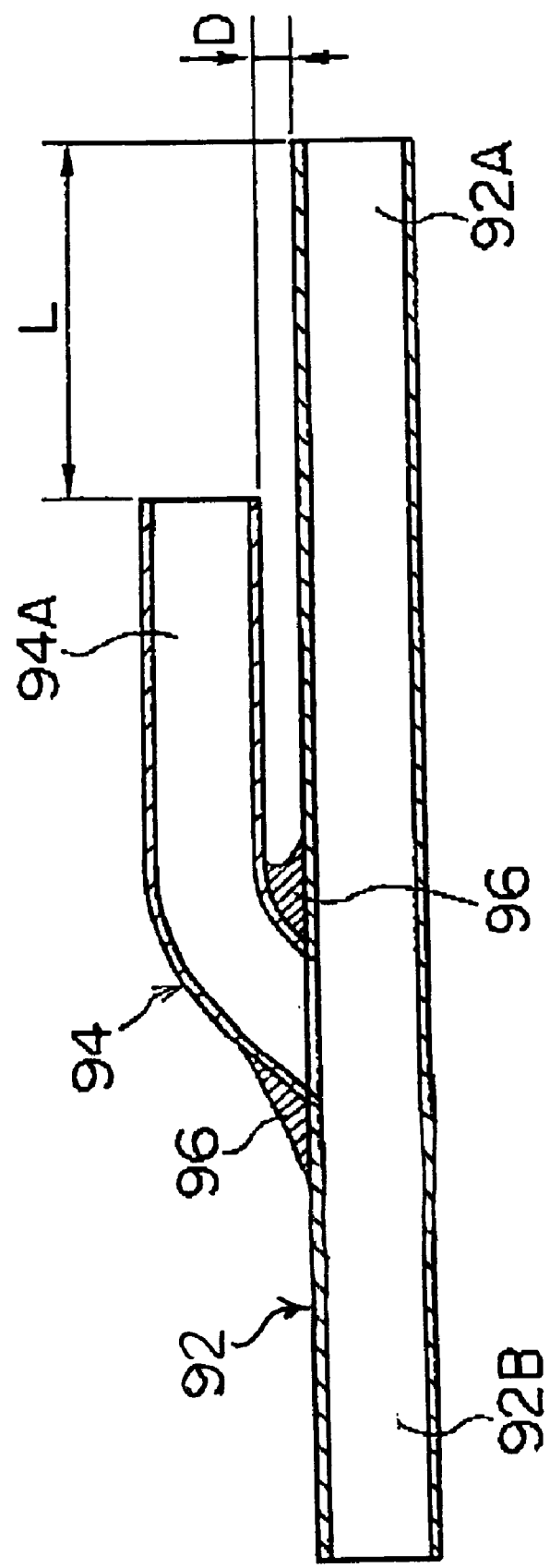
FIG. 5 is a section view of a tube joint which is different in shape from the one shown in FIG. 4.

As seen from FIG. 4, the tube joint 90 is formed in such a manner that a space D between the main tube 92 and the branch tube 94 is larger than a thickness t1 of the gas supply tube 58 and smaller than a total thickness t1+t2, where t2 is the thickness of the liquid supply tube 60.

In the tube joint 90 with the above-described structure, the liquid supply tube 60 is coupled with the outside of the end 94A of the branch tube 94, the gas supply tube 58 is coupled with the outside of the proximal end 92A of the main tube 92, and the fluid supply tube 62 is coupled with the outside of the distal end 92B of the main tube 92. Adhesive 98 such as epoxy resin is applied over the entire surface of the tube joint 90, to which the gas supply tube 58, the liquid supply tube 60 and the fluid supply tube 62 are connected. The tube joint 90 is arranged at the inside of the insertion part 16 in FIG. 1, preferably arranged at the proximity of the bending part 20 at the inside of the insertion part 16.

Now, an operation of the tube connecting structure of the endoscope of the present invention will be described.

Figure 6:
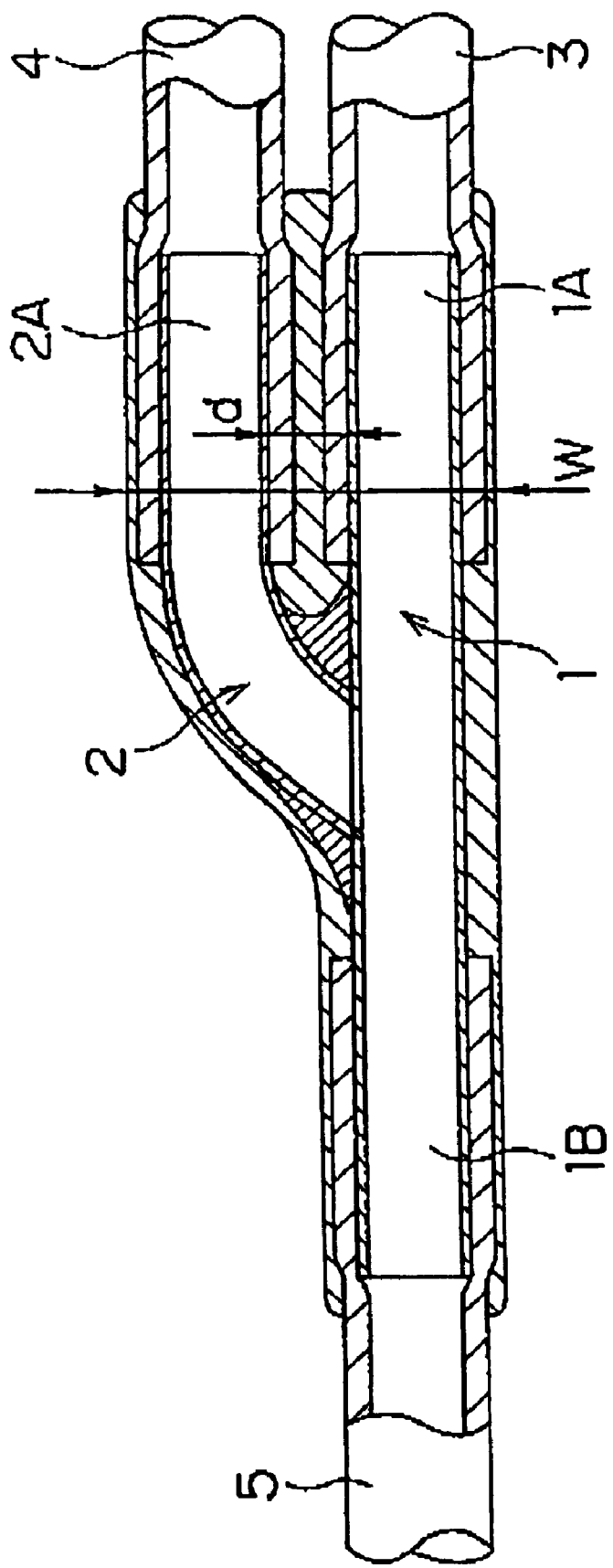
FIG. 6 is a section view of a conventional tube connecting structure.

The conventional tube joint shown in FIG. 6 is formed in such a manner as to have the end 1A of the main tube 1 and the end 2A of the branch tube 2 at substantially the same position in the longitudinal direction. For this reason, the space d between the main tube 1 and the branch tube 2 must be larger than a total thickness t1+t2, where t1 is the thickness of the gas supply tube 4 and t2 is the thickness of the liquid supply tube 5, or the gas supply tube 4 and the liquid supply tube 5 may contact with each other and they cannot be connected to the tube joint. Therefore, the space d between the main tube 1 and the branch tube 2 must be set as larger than t1+t2, and an external diameter W of the tube connecting part with the conventional tube joint is large. Hence, contents in the insertion part of the endoscope (e.g. the light guide, the forceps tube and a signal cable) become jammed therein, and durability of the contents may be shorter than expected.

In contrast to such the conventional tube joint, the tube joint 90 according to the embodiment of the present invention has the end 94A of the branch tube 94 protruding with respect to the end 92A of the main tube 92; and hence, the connecting part between the gas supply tube 58 and the main tube 92 does not come in contact with the connecting part between the liquid supply tube 60 and the branch tube 94. Therefore, the space D between the branch tube 94 and the main tube 92 can be smaller than the total thickness (t1+t2), and the external diameter W1 of the connecting part of the tubes with the tube joint 90 becomes smaller than the conventional diameter W. A filling rate of the insertion part 16 at a position of the connecting part thus decreases, and the contents in the insertion part of the endoscope are not jammed. The insertion part 16 can be narrowed as a result.

According to the tube connecting structure of the present embodiment, since the end 94A of the branch tube 94 protrudes to be longer than the end 92A of the main tube 92, the space D between the branch tube 94 and the main tube 92 can be narrowed, and the insertion part 16 can thus be narrowed.

Moreover, according to the present embodiment, since the tube joint 90 is arranged at the inside of the insertion part 16, the length of the fluid supply tube 62 is shorter than those in a case where the tube joint is arranged at the hand control part 12 or at the joint 14. Because an amount of the liquid or the gas left in the inside of the fluid supply tube 62 thereby decreases, the gas supply operation and the liquid supply operation can be quickly switched when operating the fluid supply valve 40.

In the above-described embodiment, the end 94A of the branch tube 94 of the tube joint 90 protrudes to be longer than the end 92A of the main tube 92. However, the end 92A of the main tube 92 may protrude to be longer than the end 94A of the branch tube 94; and also in this case, the space D between the main tube 92 and the branch tube 94 can be narrowed, and the insertion part 16 can also be narrowed, since the gas supply tube 58 and the liquid supply tube 60 do not interfere with each other.

Another structure is also acceptable in which the gas supply tube 58 is connected to the branch tube 94 of the tube joint 90 and the liquid supply tube 60 is connected to the main tube 92.

As described hereinabove, according to the tube connecting structure of the present invention, since a position at which the gas supply tube is connected to the tube end and a position at which the liquid supply tube is connected to the other tube end are located at different positions with respect to a longitudinal direction of the tube joint, and the space between the-ends of the two tubes can be narrowed. Therefore, durability of the contents inside improves and at the same time the insertion part is narrowed.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A tube connecting structure which is arranged at an insertion part of an endoscope, comprising:

a tube joint which has, at a first side, a first end to which a fluid supply tube is connected, and has, at a second side, a second end to which a gas supply tube is connected and a third end to which a liquid supply tube is connected, wherein a position at which the gas supply tube is connected to the second end and a position at which the liquid supply tube is connected to the third end differ in a longitudinal direction of the tube joint, and wherein a space defined between the second end and the third end is smaller than a total thickness, which is a sum of a thickness of the gas supply tube and a thickness of the liquid supply tube.

2. A tube connecting structure which is arranged at an insertion part of an endoscope, comprising:

a tube joint which has, at a first side, a first end to which a fluid supply tube is connected, and has, at a second side, a second end to which a gas supply tube is connected and a third end to which a liquid supply tube is connected, wherein a first connecting position where the gas supply tube is fitted over the second end and a second connecting position where the liquid supply tube is fitted over the third end are offset in a longitudinal direction of the tube joint so that the first connecting position and the second connecting position do not overlap.

3. The tube connecting structure as defined in claim 2, wherein a space defined between the second end and the third end is smaller than a total thickness, which is a sum of a thickness of the gas supply tube and a thickness of the liquid supply tube.

* * * * *